United States Patent [19]

Warriner

[11] Plant 4,537

[45] May 20, 1980

[54] ROSE PLANT

[75] Inventor: William A. Warriner, Tustin, Calif.

[73] Assignee: Jackson & Perkins Co., Medford, Oreg.

[21] Appl. No.: 6,644

[22] Filed: Jan. 26, 1979

[51] Int. Cl.[2] ..... A01H 5/00

[52] U.S. Cl. ..... Plt./11

[58] Field of Search ..... Plt./11

*Primary Examiner*—Robert E. Bagwill

*Attorney, Agent, or Firm*—Klarquist, Sparkman, Campbell, Leigh, Hall & Whinston

[57] ABSTRACT

An upright, vigorous, freely blooming rose plant of the hybrid tea class, characterized by its photosensitive pigment, with bud petals of Chrome Yellow and changing quickly to near Geranium Lake upon exposure to sunlight and darkening with age, with ability to maintain flower form throughout the life of the flower.

1 Drawing Figure

BACKGROUND OF THE INVENTION

The present invention relates to a new and distinct variety of rose plant of the hybrid tea class which was originated by me by crossing an unnamed variety with pollen from the variety Spellbinder, U.S. Plant Pat. No. 3,571.

The primary objective of this breeding was to produce a new rose variety of the hybrid tea class with flowers having the photosensitive pigment of Spellbinder along with a yellow pigment. This objective was substantially achieved along with other desirable improvements as evidenced by the following unique combination of characteristics which are outstanding in this new variety and distinguish it from its parents as well as from all other varieties of which I am aware:

1. An upright, vigorous, freely blooming plant.
2. A flower color which in a freshly opening bud shows petals of Chrome Yellow, changing quickly, upon exposure to sunlight, to a color near Geranium Lake and darkening with age.
3. Flower form holds well until petals drop. Outer rows of petals remain perpendicular to stem.
4. A very slight fragrance.

Asexual reproduction of this new cultivar by budding as performed at Wasco, Calif., shows that the foregoing characteristics and distinctions come true to form and are established and trasmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color terminology in accordance with Wilson's Horticultural Color Chart, except where ordinary dictionary significance of color is indicated.

Parentage: Seedling.

*Seed parent.*—Unnamed variety.

*Pollen parent.*—Spellbinder, U.S. Plant Pat. No. 3,571.

Classification:

*Botanical.*—Rosa hybrid.

*Commercial.*—Hybrid Tea.

FLOWER

Observations made from specimens grown at Irvine, Calif., September, 1978.

Blooming Habit: Continuous.

Bud:

*Size.*—1 inch when petals start to unfurl.

*Form.*—Short, blunt top.

*Color.*—When sepals first divide, near Geranium Lake (20) with areas near base of Lemon Yellow (4) overlaid with Geranium Lake (20). Petal tips occasionally very dark, near Currant Red (821). When half blown, upper sides of center petals are Chrome Yellow (605/2) changing upon exposure to Geranium Lake (20), intermediate stages are a blend of the two colors; lower sides of center petals Chrome Yellow (605/2), outer petals Chrome Yellow (605/2) overlaid with Geranium Lake (20/2).

*Sepals.*—Color: Outer surface Scheeles Green (860/3); inner surface Scheeles Green (860/3) with much white tomentum. Three appendaged sepals lightly appendaged; two unappendaged sepals hairy edged.

*Receptacle.*—Color: Scheeles Green (860); shape: funnel; size: medium, broad: surface: glandular-pubescent.

*Peduncle.*—Length: short; surface: glandular-pubescent; color: light green; strength: stiff, erect.

*Opening.*—Petals fold out without curling. Outer petals hold a position perpendicular to stem.

Bloom:

*Size.*—Medium. Average open size 4 inches.

*Stems.*—Long.

*Borne.*—Singly and several together.

*Form.*—When first open: high center. Permanence: retains its form to the end.

*Petalage.*—Number of petals under normal conditions: 28 to 30.

*Color.*—Center of flower: upper side of petals Chrome Yellow (605/2) when freshly opened. Reverse side of petals Chrome Yellow (605/2). Outer petals: Geranium Lake (20/2) where exposed longest to sunlight. Base of petals: near Sulphur Yellow (1). General Tonality from a distance - blend of Chrome Yellow (605/2) and Geranium Lake (20/2).

*Variegations.*—Occasionally has very dark areas on edges near Currant Red (821).

*Discoloration.*—Third day: All exposed areas become near Geranium Lake (20).

*Fragrance.*—Slight.

Petals:

*Texture.*—Thick.

*Shape.*—Round.

*Form.*—Tips slightly recurved.

*Arrangement.*—Imbricated. Petaloids in center, few, sometimes fused with filaments.

*Persistence.*—Drop off cleanly.

*Lastingness.*—On the plant, very long. As cut flower, very long.

Reproductive parts:

*Stamens, anthers.*—Medium. Color: yellow. Arrangement: fused with petaloids, occasionally.

*Filaments.*—Reddish except yellow when fused with petaloids.

*Pollen.*—Gold yellow.

*Styles.*—Color: Red.

*Stigmas.*—Color: white to very pale green.

PLANT

Form: Bush.

Growth: Very vigorous, upright.

Foliage: Number of leaflets on normal mid-stem leaves 5 or 7.

*Size.*—Medium.

*Quantity.*—Normal.

*Color.*—New foliage: Garnette Brown (00918/3); old foliage: Spinach Green (0960).

*Shape.*—Wide, elliptic.

*Texture.*—Leathery.

*Edge.*—Serrated, slightly undulated.

*Serration.*—Single, small.

*Petiole.*—Rachis: Color, reddish; underside, prickles, sometimes smooth.

*Stipules.*—Long and wide, edges glandular.

*Disease resistance.*—Normally resistant to mildew, under normal growing conditions at Irvine, Calif.

Wood:

*New wood.*—Color: reddish. Bark: smooth.

*Old wood.*—Color: green. Bark: smooth.

Prickles:

*Quantity.*—On main stalks from base: ordinary. On laterals from stalk: ordinary.

*Form.*—Long, narrow base, hooked downward.

*Color when young.*—Red.

*Position.*—Irregular.

Small prickles: None.

I claim:

1. A new and distinct variety of rose plant of the hybrid tea class, substantially as herein shown and described, characterized particularly as to novelty by its upright, free blooming plant, Chrome Yellow changing to Geranium Lake flower color, its ability to maintain flower form throughout the life of the flower and by its very slight fragrance.

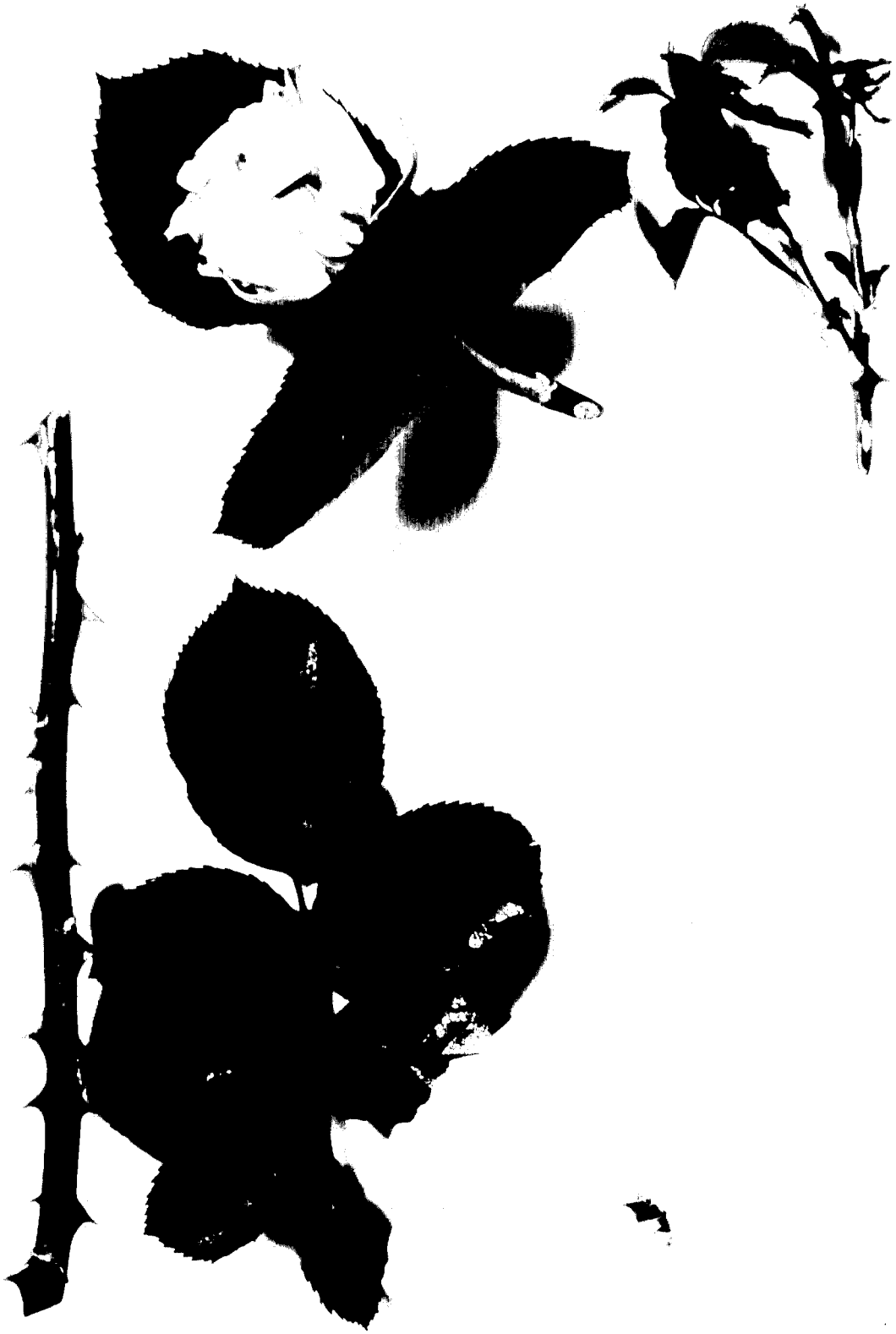

* * * * *